United States Patent [19]

DeOca et al.

[11] Patent Number: 4,785,676
[45] Date of Patent: Nov. 22, 1988

[54] ASEPTIC SAMPLE FITTING

[76] Inventors: Henry M. DeOca, 1596 S. Bend La., Lakeview, N.Y. 14085; Robert C. McNally, 57 Adamwood Dr., East Aurora, N.Y. 14052

[21] Appl. No.: 86,798

[22] Filed: Aug. 19, 1987

[51] Int. Cl.$^4$ ............................................. G01N 1/10
[52] U.S. Cl. .................................. 73/863.85; 141/329
[58] Field of Search ....................... 73/863.85, 864.86; 141/1, 2, 18, 69, 83, 98, 234, 329, 330

[56] References Cited

U.S. PATENT DOCUMENTS

| | | | |
|---|---|---|---|
| 3,776,042 | 12/1973 | Werra et al. | 73/863.85 |
| 3,779,082 | 12/1973 | Galloway | 73/863.85 |
| 3,985,016 | 10/1976 | Haraki | 73/864.86 |
| 4,056,981 | 11/1977 | Kalka et al. | 73/863.85 |

Primary Examiner—Mark J. Thronson
Attorney, Agent, or Firm—Christel, Bean & Linihan

[57] ABSTRACT

An aseptic sampler fitting including a conduit portion for in-line connection between two pipes containing a viscous fluid, a neck portion associated with the conduit portion defining an access opening therein providing access to the interior of the conduit portion, and a cover being securable to the neck portion for covering the access opening defined therein utilizes a gasket positionable between the neck portion and the cover for maintaining a complete physical separation between the cover and the neck portion. The components of the fitting are smoothly-surfaced to facilitate cleaning of the fitting, and the cover includes a plurality of pierceable, self-closing elastomeric stoppers permitting the insertion through the cover of a hypodermic needle or the like for the purpose of extracting a sample of fluid contained within the conduit portion. The cover is constructed of components facilitating ease of replacement of the elastomeric stoppers. Furthermore, the conduit portion and neck portion are joined so as to form a Tee-like arrangement.

14 Claims, 2 Drawing Sheets

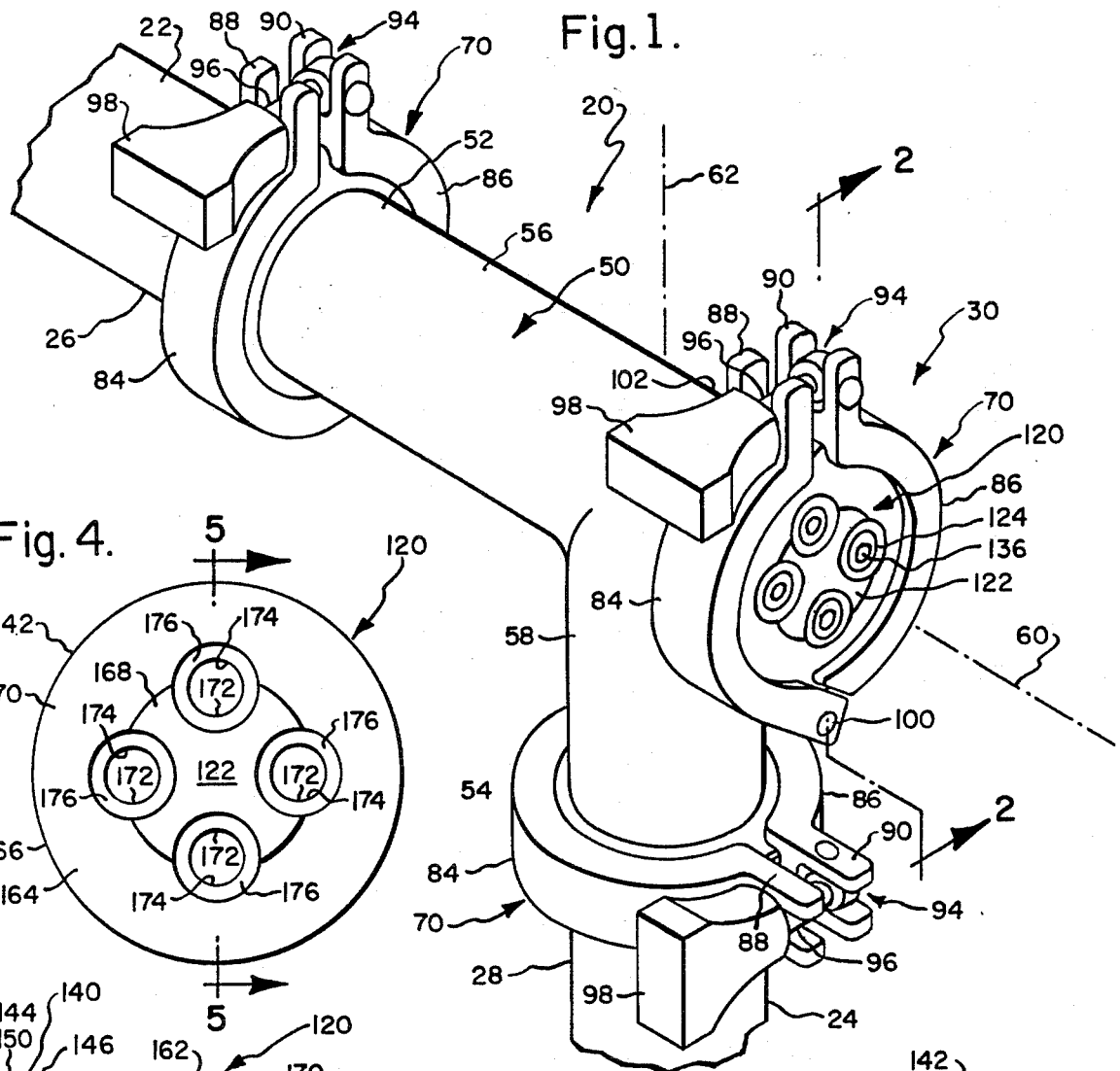
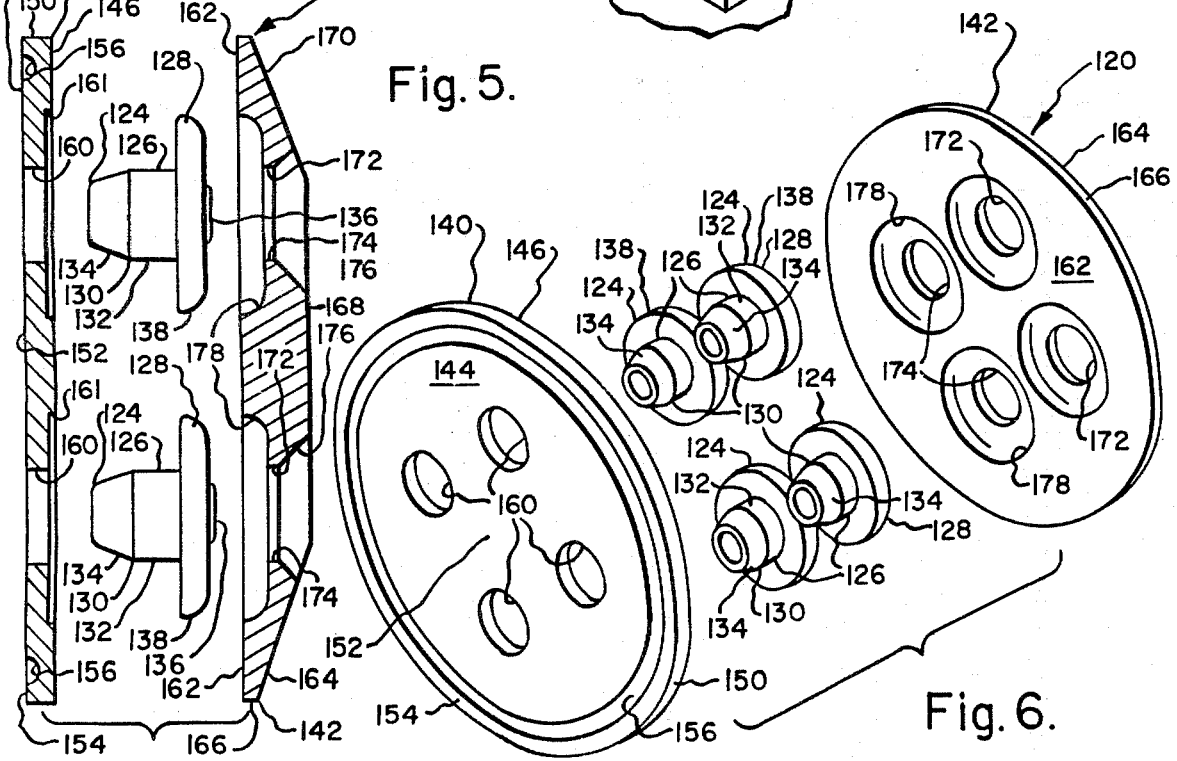

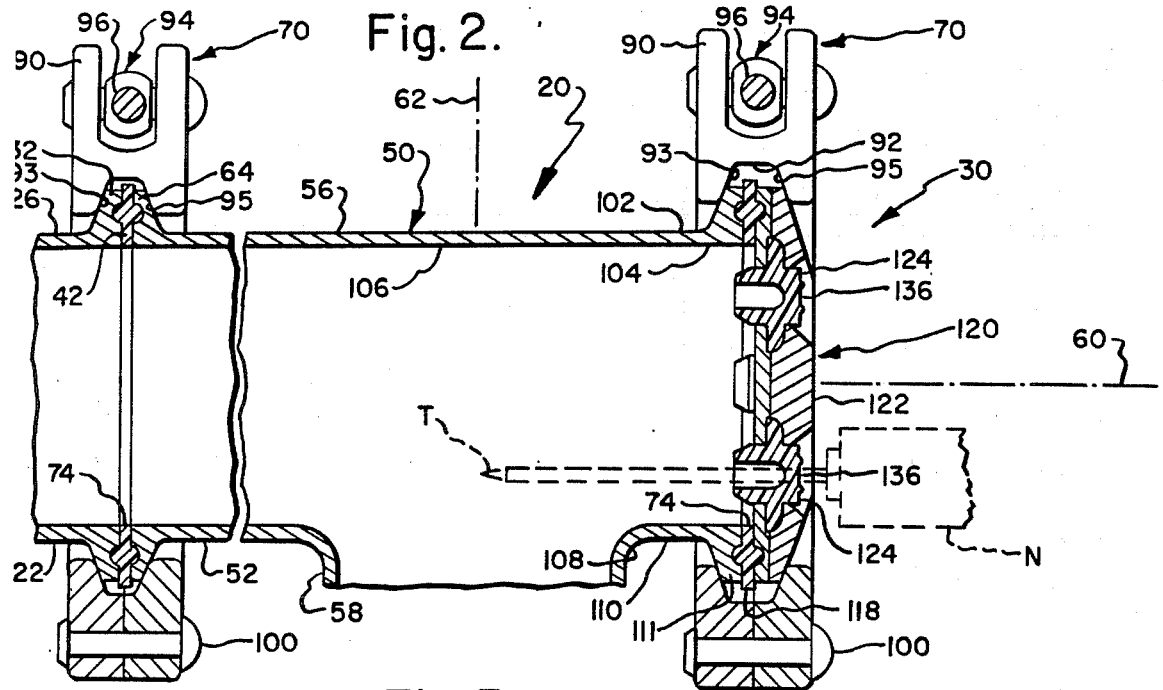
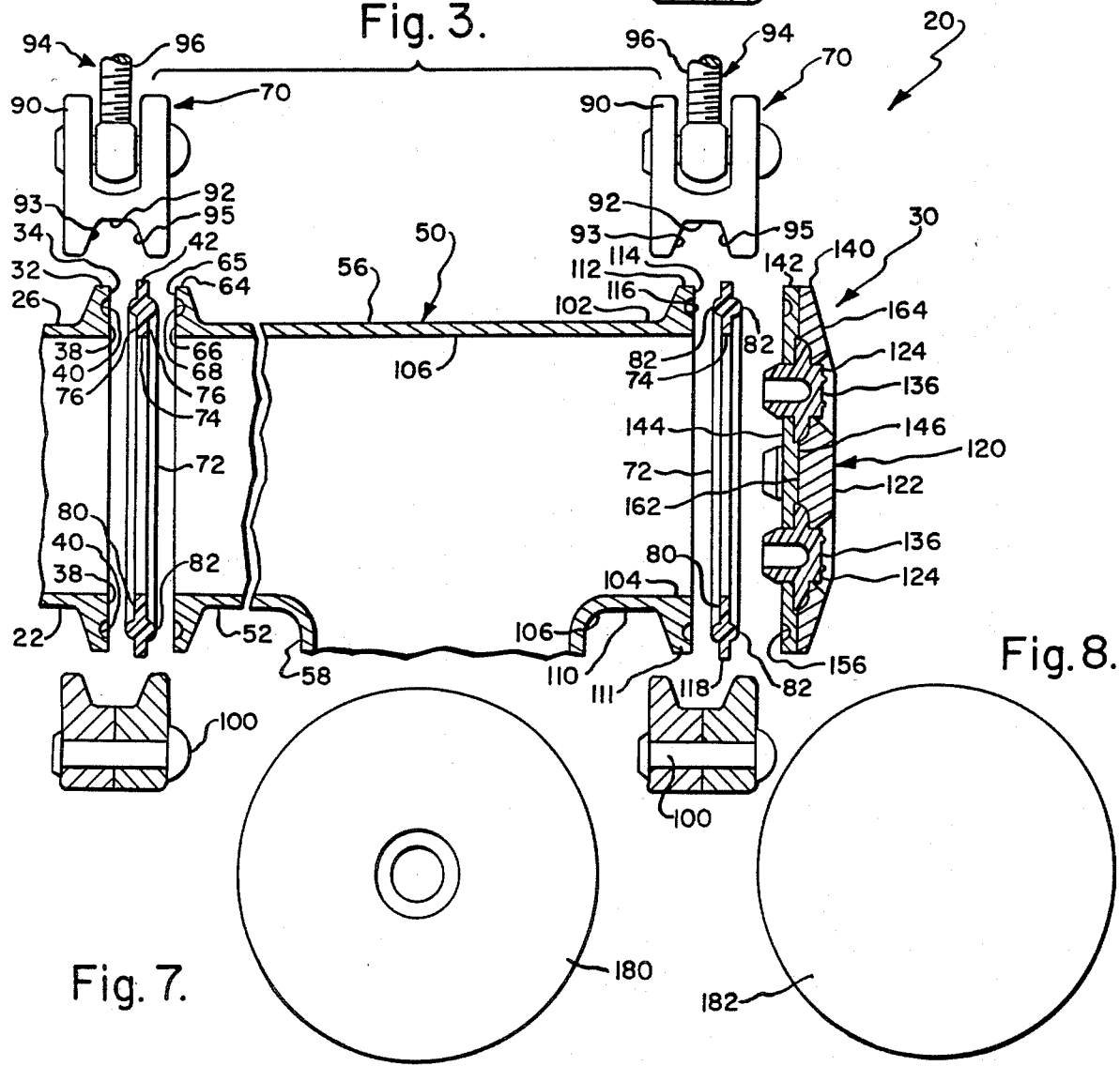

ASEPTIC SAMPLE FITTING

BACKGROUND OF THE INVENTION

This invention relates generally to a fitting for piping associated with a fluid tank, line or other enclosure and relates more particularly to an aseptic sample fitting through which samples of fluid contained within the piping can be extracted.

In the production of viscous products, such as consumable fluids or various pharmaceuticals, in which the bacteria count must be maintained within predetermined levels, samples of the products are commonly taken at appropriate stages of the product production. Inasmuch as the products are commonly routed through a piping network joining the stages of production, sample fittings can be incorporated into the piping for the purpose of providing an access port through which samples of the product can be extracted. Such a sample fitting commonly includes a conduit portion attachable in-line with the piping and a neck portion joined to the conduit portion. The neck portion defines an opening therein providing access to the product contained within the conduit portion, and a cover is operatively securable to the neck portion for closing the access opening defined therein. Commonly, the cover includes a pierceable, self-closing membrane which permits the insertion of a hypodermic needle or similar instrument therethrough for the purpose of extracting a product sample from the conduit portion without removing the cover. An example of a fitting having a neck portion and cover of the aforedescribed type is shown and described in U.S. Pat. No. 3,779,082.

Inasmuch as it is desirable for sanitation purposes that the fitting be at all times relatively clean, a limitation associated with conventional sample fittings such as the one described in the referenced patent relates to the capacity of the neck portion thereof to be maintained clean. For example, the neck portion and cover of the fitting described in the referenced patent are in direct engagement with one another by means of a threaded connection. It has been found that the thread grooves of such a threaded connection provide collection channels for the accumulation of the viscous product when, due to product spillage or otherwise, the outer surface of the neck portion is exposed to the product. If, of course, viscous product is permitted to collect within the thread grooves, bacteria spawned therein could contaminate the product contained within the fitting conduit portion and the piping within which the fitting is connected.

Another limitation associated with a fitting such as the one described in the referenced patent relates to the relatively high cost of the pierceable membrane supported within the fitting cover. Such a high cost is believed to be due, at least in part, to the relatively large quantity of material contained within the body of the membrane. Furthermore, inasmuch as the membrane is commonly replaced with a new one between selected product processing cycles, the relatively high cost of the membrane contributes to a relatively high maintenance cost of the fitting.

Accordingly, it is an object of the present invention to provide a new and improved sampler fitting through which a sample of a viscous product can be extracted.

Another object of the present invention is to provide such a fitting wherein the cleanliness thereof can be easily maintained.

Still another object of the present invention is to provide such a fitting having components absent of thread grooves in which the viscous product is apt to collect.

Yet still another object of the present invention is to provide such a fitting wherein the cover thereof is maintained out-of-contact with the neck portion.

A further object of the present invention is to provide such a fitting including a pierceable, self-closing membrane which can easily be replaced and which is relatively inexpensive.

A still further object of the present invention is to provide such a fitting which is economical to construct and effective in operation.

SUMMARY OF THE INVENTION

This invention resides in a sampler fitting for in-line connection between two pipes.

The fitting is comprised of means defining a conduit, means defining a neck portion associated with the conduit means, a over, and gasket means. The conduit means has two opposite ends which are each adapted to be connected to a corresponding one of two pipes in a pipeline so that fluid exiting one of the pipes is directed into the other of the pipes through the conduit means. The neck portion defines an opening providing access to the interior of the conduit means, and the cover is adapted to cover the access opening of the neck portion. The gasket means are positionable between the cover and the neck portion for maintaining a complete physical separation between the cover and the neck portion. Further, the fitting includes clamping means for clamping the cover over the access opening with the gasket means operatively positioned between the cover and the neck portion.

In one embodiment of the fitting, the cover includes plate means and at least one pierceable, self-closing membrane or stopper constructed of an elastomeric material. The plate means include two platen members positioned in a face-to-face arrangement and including aligned openings therethrough defining at least one opening through the plate means. The stopper includes a body portion positioned between the platen members so as to span the opening of the plate means and so that when the cover is operatively secured to the neck portion and across the access opening, the stopper is tightly held between the two platen members.

BRIEF DESCRIPTION OF THE DRAWING FIGURES

FIG. 1 is a perspective view of an embodiment of the present invention shown operatively positioned in line with the piping of a fluid line.

FIG. 2 is a fragmentary cross-sectional view taken about on lines 2—2 in FIG. 1.

FIG. 3 is a view similar to that of FIG. 2, shown exploded.

FIG. 4 is an elevation view of the cover of the FIG. 1. embodiment as seen generally from the right in FIG. 3.

FIG. 5 is a cross-sectional view taken about on lines 4—4 of FIG. 4.

FIG. 6 is a perspective view of the FIG. 5 cover, shown exploded.

FIG. 7 is a view similar to that of FIG. 4 illustrating an alternative cover for a fitting in accordance with the present invention.

FIG. 8 is a view similar to that of FIG. 4 illustrating another alternative cover for a fitting in accordance with the present invention.

DETAILED DESCRIPTION OF THE ILLUSTRATED EMBODIMENTS

Turning now to the drawings in greater detail and considering first FIG. 1, there is illustrated an embodiment, generally indicated 20, in accordance with the present invention shown operatively connected to two pipes 22,24. The pipes 22,24 are part of a piping network of the type commonly utilized to connect two processing or production stages involving viscous fluids, such as milk, fruit juice or another consumable food product in fluid form, and illustrates an exemplary environment in which the fitting 20 is used.

The pipes 22 and 24 are each cylindrical in form with attachment end portions 26 and 28, respectively, and are arranged in relationship to one another so that the longitudinal axes of the end portions 26,28 are oriented perpendicular to one another. As will be explained in greater detail hereinafter, the fitting 20 is operatively connected in-line between the pipes 22,24 so that fluid flowing through the pipes 22,24 must pass through the fitting 20. For purposes of extracting a sample of fluid contained within the fitting 20, the fitting 20 includes access means, generally indicated 30, providing access to the interior of the fitting 20.

With reference to FIGS. 2 and 3 and as exemplified by the end portion 26 of pipe 22, each pipe end portion 26 or 28 terminates in a radially outwardly-directed flange 32 having an edge surface 34 which generally faces axially of the pipe. The edge surface 34 includes a flat portion 38 oriented in a radial plane of the pipe 22 and a circular detent or groove 40 located generally centrally of the flat portion 38 as shown so as to encircle the corresponding pipe end opening. The walls of the groove 40 are generally rounded in shape so as to provide an indentation of generally C-shaped cross section wherein the C opens generally axially of the pipe. The edge surface 34 of each pipe end portion 26 or 28 coacts with a gasket 42, hereinafter described, to seal the fitting 22 to the pipes 22 and 24.

With reference to FIGS. 1-3 and in accordance with the present invention, the fitting 20 includes means, generally indicated 50, defining a conduit having two opposite ends 52,54 adapted to be connected between the two pipes 22,24 so that fluid exiting one of the pipes 22 or 24 is routed into the other of the pipes 22 or 24 through the conduit means 50. The conduit means 50 includes two straight pipe-like sections 56,58 appropriately joined to one another so that the longitudinal axes, indicated 60,62, respectively, of the straight sections 56,58 are oriented at a right angle. Each straight section 56 or 58 is cylindrical in form and terminates in a circular opening at the corresponding end 52 or 54. The conduit means 50 are constructed of stainless steel but can be constructed of any of a number of suitable materials.

As exemplified by the end portion 56 illustrated in FIG. 3, each conduit straight section 56 or 58 includes a radially outwardly-directed flange 64 at the corresponding end 52 or 54. As does the flange 32 of the pipe 22, each conduit flange 64 defines an edge surface 65 as shown which generally faces axially of the corresponding conduit straight section 56 or 58. Furthermore, each flange edge surface 65 includes a flat portion 66 oriented in a radial plane of the straight section 56 or 58 and defines a detent in the form of a circular groove 68 located generall centrally of the flat portion 66 and encircling the opening defined in the corresponding conduit end 52 or 54. As best shown in FIG. 3, the walls of each groove 68 are rounded so as to provide an indentation of generally C-shaped cross section with the C of the indentation opening generally axially of the corresponding straight section 56 or 58.

For purposes of sealingly clamping the conduit means 50 to the pipes 22,24, there are provided a gaskets 42 (only one shown in FIGS. 2 and 3), introduced earlier, and a pair of clamps 70. Each gasket 42 is in the form of a ring-like body 72 of suitable gasketing material, such as rubber or a suitable elastomeric material, for providing an impermeable seal between the clamped flanges 32 and 64 and defining a central opening 74 which is aligned with the openings in the corresponding pipe and conduit straight section ends. The gasket body 72 defines two opposite side surfaces 76,78 for engaging the flanges 32,64 when clamped therebetween, which side surfaces 76,78 are generally shaped in conformity to the contours or shape of the corresponding flange edge surface 34 or 65 which the side surfaces 76,78 are adapted to engage. To this end, each side surface 76 or 78 defines a flat portion 80 for engaging the flat portion 34 or 66 at the flanges 32 or 64 and defines a bead 82 encircling the central opening 74 of generally rounded or C-shaped cross section which protrudes generally from the plane of the corresponding flat portion 80. When the flanges 32,64 and gasket 42 are operatively clamped together, the beads 82,82 are received by so as to substantially fill the flange grooves 40,68 and the flat portions 80,80 of the gasket body 72 flatly engage the flat portions 38,66 of the flanges 32,64.

With reference again to FIGS. 1-3, each clamp 70 is of a type commonly known as a tri-clamp having a construction which is well-known in the art. Briefly, each clamp 70 includes two arcuate members 84,86 pivotally joined together at one end thereof by means of a pin 100 and includes radially outwardly-directed flanges 88,90 at the other end thereof. When the arcuate members 84,86 are positioned so that the flanges 88,90 thereof are relatively close together, the arcuate member 84,86 collectively provide a ring having an inwardly-opening annular groove 92 for encircling the abutting flanges 32,64 and gasket 42. As best shown in FIG. 2, the groove 92 defines generally opposing surfaces 93,95 for pressingly engaging the flanges 32,64 when the clamp flanges 88,90 are moved toward one another.

With reference still to FIG. 1 and shown extending between the clamp flanges 88,90 is a screw and nut arrangement 94 for selectively tightening or loosening the clamp 70. One end of the arrangement screw, indicated 96, is pivotally fastened to the clamp flange 90 and the other end of the screws 96 threadably receives a hand-manipulable nut 98.

By selectively tightening or loosening the nut 98 upon the screw 96 so that the nut 98 presses against or backs away from the clamp flange 88, the opposing surfaces 94,96 of the clamp groove 92 selectively compress the flanges 32,64 toward one another or relieve clamping pressure from the flanges 32,64. When the clamp 70 is operatively clamped about the flanges 32 and 64 as shown in FIG. 2, the gasket 42 is in a compressed condition so that the seal provided between the engaging surfaces of the pipe flange 32 and the gasket 42 and between the conduit flange 64 and the gasket 42 is thereby enhanced.

With reference again to FIGS. 1-3, the access means 30 of the fitting 20 includes a neck portion 102 joined to the conduit means 50 and defining a circular access opening 104 providing access to the interior, indicated 106, of the conduit means 50. In the fitting embodiment 20, the neck portion 102 is effectively an extension of the cylindrical conduit straight section 56 opposite the conduit portion end 52. Hence, the conduit means 50 and neck portion 102 collectively resemble a Tee fitting.

The neck portion 102 defines a end portion 110 terminating in a radially outwardly-directed flange 111 having an edge surface 112 which generally faces axially of the end portion 110. The edge surface 112 includes a flat portion 114 oriented in a radial plane of the end portion 110 and a detent in the form of a groove 116 located generally centrally of the flat portion 114 and encircling the opening 104. The size and shape of the flange 111 and its attending edge surface 112 are identical to that of the conduit flange 64 and its edge surface 65. As will be apparent hereinafter, the flange 111 coacts with a gasket 118 when the access opening 104 is operatively closed.

Furthermore, the length of the neck portion 102 as measured from the flange end or edge surface 11 is relatively short in comparison to the length of the straight sections 56 or 58. Inasmuch as a hypodermic needle, indicated N in FIG. 2, or similar instrument is inserted through the access opening 104 for the purpose of extracting a product sample from the interior 106 of the conduit means 50, it is preferred that the neck portion 102 be relatively short as aforesaid so that the tip T of the needle N is positioned at approximately the center of the flow of fluid moving through the conduit means 50 when the needle N is fully inserted. Hence, the sample extracted through the needle N will be taken from substantially the center of the fluid flow. Furthermore, inasmuch as clean-in-place operations involve a purging of the pipes 22,24 with a cleansing fluid such as a suitable detergent, it has been found that a relatively short neck-portion is more effectively cleaned by clean-in-place operations than is a relatively long neck portion. In the fitting embodiment 20, the length of the neck portion 102 as measured between the flange edge surface 112 and the location, indicated 108, of the junction between the neck portion 102 and the conduit end portion 58 is about 0.5 inches (1.7 cm).

In accordance with the present invention, the fitting 20 further includes a cover, generally indicated 120, for covering the access opening 104. As best shown in FIGS. 2 and 3, the cover 102 includes plate means 122 constructed of stainless steel or another suitable material and a plurality of pierceable membranes or stoppers 124,124 supported within the plate means 122. Each stopper 124 is comprised of a body 126 constructed of an elastomeric material such as synthetic rubber, possessing a degree of resiliency for closing a needle-formed puncture extending therethrough upon extraction of the needle N (FIG. 2) from the stopper 124. Furthermore, the material comprising each stopper 124 is chemically inert with regard to the fluid flowing through the conduit means 50.

With reference to FIG. 6, the body 126 of each stopper 124 includes a flange or platen portion 128 having a somewhat cylindrical periphery and a nipple portion 130 joined centrally of and extending from one side of the platen portion 128. The nipple portion 130 includes a section adjacent the platen portion 128 which defines a cylindrical surface 132 and an end section which defines a frustoconical surface 134. For a reason which will be hereinafter apparent and as best shown in FIG. 5, the platen portion 128 includes a central section 136 and border section 138 bordering the central section 136.

The plate means 122 of the cover 120 includes two platen members 140,142 arranged in a face-to-face or overlying relationship with one another as shown in FIGS. 2 and 3. As best shwon in FIG. 6, the platen member 140 defines two opposite planar side faces 144,146 and a cylindrical edge 148. The platen member 140 further includes a central section 152 and a border section 154 bordering the central section 156. Defined in the border section 154 and on the face 144 thereof is a ring-like indentation in the form of a groove 156 encircling the central portion 152. As shown in the cross-sectional view of FIG. 3, the groove 152 is arcuate in shape so as to provide the groove 152 with a rounded or C-shaped cross section. As will be apparent hereeinafter, the groove 152 is adapted to accept the bead 82 of a gasket 158 when the platen member face 144 is operatively placed in engagement with the gasket 158.

With reference again to FIG. 6, the platen member 140 defines four circular through-openings 160,160 extending between the faces 144,146 and located in the central portion 152 of the member 140. The openings 160,160 are each slightly smaller in diameter than that of the cylindrical surface 132 of the stopper nipple portion 130 so that when the nipple portion 130 is operatively inserted into the opening 160, the cylindrically-surfaced section of the nipple portion 130 is snugly received by and thereby securely retained within the opening 160. As best illustrated in FIG. 4 the openings 160,160 are disposed over the platen member face 146 in a regular pattern. Defined in the platen side face 146 are four relatively circular recesses 161,161 each arranged so as to be substantially centered about a corresponding opening 160. The diameter of each recess 161 is of such size to receive part of the stopper platen portion 128 when the nipple portion 130 is operatively accepted by the opening 160.

With reference to FIGS. 4-6, the platen member 142 includes two opposite side faces 162,164 and a cylindrical edge 166. The side face 162 is generally planar, and the side face 164 includes a generally planar central section 168 and a beveled border section 170 bordering the central section 168. Extending between the side faces 162,164 are four through-openings 172,172 which are aligned with the through-openings 160,160 of the platen member 140 when the cover 120 is assembled. Each through-opening 160 has a portion having a cylindrical surface 174 and an end portion having a conical or funnel-like surface 176. Defined in the side face 162 of the platen member 142 are four circular recesses 178,178 each arranged so as to substantially centered about a corresponding through-opening 172 and each adapted to receive the stopper platen portion 128 when the cover 120 is assembled. In this connection, the diameter of each recess 178 is slightly smaller than that of the stopper platen portion 128 which it is adapted to accept so that when the platen portion 128 is operatively inserted therein, the platen portion 128 is snugly received by and thereby securely retained within the recess 178. It will be understood from the foregoing that when the cover 120 is assembled, the snug fit-up relationship between each opening 160 and the stopper nipple portion 128 received thereby and between each recess 178 and the stopper platen portion 128 effective holds the cover components together as a single unit.

With reference again to FIGS. 2 and 3 and for purposes of sealing the cover 120 over the neck portion 104, there is positionable between the neck portion flange 111 and the cover 120 a gasket 118, introduced earlier. The gasket 118 is identical in construction to the gasket 42 described above and accordingly its components bear the same reference numerals. When the cover 120 and gasket 118 are operatively positioned over or about the access opening 104 as illustrated in FIG. 2, the beads 82,82 of the gasket 118 are received by the ring-like grooves 116 and 156 of the flange 111 and cover member 140, respectively.

The fitting 20 further includes a clamp 70 for operatively clamping the cover 120 over the opening 104. The clamp 70, described earlier, includes opposing surfaces 93,94 adapted to press flange 111 and cover 120 toward one another at the periphery thereof when the clamp 70 is tightened to thereby sealably clamp the cover 70 upon the neck portion 102. Because the gasket 118 is placed in a compressed condition between the flange 11 and cover 120 when the clamp 70 is tightened thereabout, the seal provided between the engaging surfaces of the flange 111 and gasket 118 and between the gasket 118 and cover member 140 is effectively enhanced. Similarly, the platen portions 128,128 of the stoppers 124,124 are placed in a compressed condition between the cover members 140,142 when the clamp 70 is tightened about the flange 111 and cover 120 as aforedescribed so that the seal provided by the stopper platen members 128,128 with the cover member faces 146 and 162 is effectively enhanced.

When operatively clamped to the neck 102 as illustrated in FIGS. 2 and 3, the central or opening-defining section of the cover platen members 140,142 is aligned with the access opening 104. Hence, the stoppers 124,124 are positioned in alignment with the opening 104. It follows that operative insertion of a hypodermic needle N (FIG. 2) through any of the stoppers 178 positions the needle tip T generally centrally of the conduit means 50 for purposes of extracting a sample therefrom.

It will be understood from the foregoing that the gasket 118 maintains a complete physical separation between the neck portion 102 and the cover 120 when the two are operatively clamped together. Such a separation is believed to inhibit any transfer or migration of bacteria from the cover 120 to the neck portion 104 and thereby reduce the likelihood of a contamination of fluid contained within the conduit means 50 by the cover 120.

Furthermore and as best illustrated in FIGS. 2, 3 and 5, each component of the fitting 20 is relatively smoothly-surfaced so as not to define locations where fluid is likely to collect and so as to provide surface which can be cleaned with relative ease. In contrast, conventional fittings having covers which are threaded upon the neck portions thereof include threaded grooves which are relatively difficult to clean and provide fluid-collection locations which bacteria is likely to spawn. Therefore, the relatively smooth surfaces of the components of the fitting 20 are believed to facilitate cleaning and the maintenance of the fitting 20.

An advantage provided by the cover 120 relates to the ease with which the stoppers 124,124 can be replaced when desired. Commonly, the stoppers 124,124 are replaced between preselected processing cycles and when no fluid is contained within the pipes 22,24 and conduit means 50. In order to replace a stopper 124, the clamp 70 is initially removed from the flange 111 and cover 120 and the cover 120 is removed from engagement with the gasket 118. The cover platen members 140,142 are then separated from one another and the stoppers 124,124 are pulled from the platen members 140,142. At that point, new stoppers each having a construction like that of stopper 124 are inserted nipple-end first through the platen member openings 160,160, and the cover 120 is reassembled and reclamped against the gasket 118 and neck portion 102 with the clamp 70. Inasmuch as the body of the stoppers 124,124 contain a relatively small amount of material and are relatively uncomplicated in construction, the stoppers 124,124 are relatively inexpensive to replace. Hence, the cost of the stoppers 124,124 do not appreciably contribute to the maintenance cost of the fitting 20.

It will be understood that numerous modifications and substitutions can be had to the aforedescribed embodiments without departing from the spirit of the invention. For example, although the cover 120 of the fitting 20 has been shown and described above as including four stoppers 124,124, a fitting cover in accordance with this invention may have any number of or no stoppers. For example, there is illustrated in FIG. 7 a cover 180 for an alternative fitting of this invention including a single stopper 124 disposed centrally in one side face thereof. Furthermore, there is illustrated in FIG. 8 a fitting cover 182 including no stoppers. The cover 182 may be preferred over a stopper-including cover as a means for capping off the neck portion 102 and thereby provide relatively permanent cover for a fitting. The covers 120,180 and 182 of FIGS. 4, 7 and 8, respectively, possess sufficient structural similarities in size and shape that each can be selectively interchanged with one another and are believed to be advantageous in this regard.

Still further, although the conduit means 50 of the fitting embodiment 20 of FIGS. 1-6 has been shown and described as being in the form of a L-shaped elbow, conduit means in accordance with the broad aspects of this invention may be in the form of an arcuate or C-shape pipe adapted to be joined at its opposite ends to pipeline pipes, such as the ones indicated 22 and 24 in FIG. 1. Accordingly, the aforedescribed embodiment 20 of FIGS. 1-6 is intended for the purpose of illustration and not limitation.

We claim:

1. A sampler fitting for in-line connection between two pipes comprising:

means defining a conduit having two opposite ends each adapted to be connected to a corresponding one of the two pipes so that fluid exiting one of the pipes is directed into the other of the pipes through said conduit-defining means;

means defining a neck portion associated with said conduit-defining means, said neck portion having an opening providing access to the interior of the conduit of said conduit-defining means;

a cover for covering said access opening;

gasket means positionable between said neck portion and said cover for maintaining a complete physical separation between said cover and said neck portion, said gasket means defining a central opening therethrough which is aligned with said access opening when operatively positioned in engagement with said neck portion; and clamping means for operatively clamping said cover over said access opening with said gasket means operatively positioned between said neck portion and said cover, said cover including two platen members positioned in a face-to-face arrangement with one another and each having a central portion and a boundary portion bordering the central portion of the corresponding platen member, the central portion of each platen member defining a through-opening which is aligned with the through-opening of the other platen member and the central opening of the gasket means when said cover is operatively clamped to said neck portion, said cover further including means defining a pierceable, self-closing stopper having a body of elastomeric material and of relatively small mass in comparison to the mass of the platen members and associated with said platen members so that the stopper body generally spans the aligned through-openings of the platen members and so that a hypodermic needle or the like can be directed through the stopper body and into the interior of said neck portion for the purpose of extracting a sample amount of fluid flowing through the conduit of said conduit-defining means, said stopper body having a platen portion and a nipple portion joined centrally of and extending from one side of the platen portion, the through-opening of one platen member snugly accepting the nipple portion of the stopper body so that the stopper body is securely retained within said one platen member as surfaces of the nipple portion pressingly engage the walls of the through-opening of said one platen member, the central portion of the other platen member having a side face which generally faces said one platen member and including a detent in the form of a recess defined in said side face and located about the through-opening of said other platen member, said recess snuggly accepting the platen portion of the stopper body so that the stopper body is securely retained within said other platen member as surfaces of the platen portion pressingly engage the walls of the recess of said other platen member and so that the platen members are held in the aforesaid face-to-face arrangement and in an assembled condition as each platen member is retainably secured to the stopper.

2. A sampler fitting as defined in claim 1 wherein each of said neck portion and said cover define relatively smooth surfaces to facilitate cleaning of the neck portion and cover.

3. A fitting as defined in claim 1 wherein said neck portion is generally cylindrical in form and defines an edge surface generally encircling said access opening and facing generally axially thereof, said cover defines a peripheral edge surface which is positionable so as to face said access opening edge surface, said gasket means includes a generally ring-like body positionable between said access opening edge surface and said cover edge surface so that when said cover is operatively clamped to said neck portions, said ring-like body sealingly engages said neck portion edge surface and sealingly engages said cover edge surface.

4. A fitting as defined in claim 3 wherein said ring like body has one side surface for engaging said neck portion edge surface and another side surface opposite said one side surface for engaging said cover edge surface, said one side surface generally shaped in conformity to the shape of said neck portion edge surface and another side surface shaped generally in conformity to the shape of said cover edge surface to thereby enhance the effective sealing between said ring-like body and said neck portion edge surface and between said ring-like body and said cover edge surface.

5. A fitting as defined in claim 4 wherein at least one of said neck portion edge surface and said cover edge surface defines a detent encircling said access opening and the corresponding side surface of said ring-like body includes a bead portion extending therefrom and adapted to be cooperatively received by said detent when said cover is operatively clamped to said neck portion.

6. A fitting as defined in claim 1 wherein said neck portion is relatively short in length as measured from the neck portion edge surface.

7. A fitting as defined in claim 6 wherein said neck portion is no longer than about 0.5 inches (1.8 cm).

8. A fitting as defined in claim 1 wherein the central portions of the platen members of said cover define a plurality of aligned through-openings which are aligned with said access opening when said cover is operatively clamped to said neck portion and said cover includes a plurality of pierceable, self-closing elastomeric stoppers supportedly carried by and disposed across the central portions of the platen members so that each stopper spans a corresponding one of the aligned through-openings and so that each of said stoppers is physically separated from every other stopper of the cover.

9. A fitting as defined in claim 1 wherein the conduit of said conduit-defining means includes two opposite end portions, each of said end portions defining a corresponding end of said conduit, being generally straight and being arranged at generally a right angle to the other conduit end portion.

10. A fitting as defined in claim 9 wherein said neck portion is an extension of said one straight end portion of said conduit opposite the corresponding conduit end so that said conduit and neck portion resemble a Tee fitting.

11. An aseptic sampler fitting having a conduit portion adapted to be connected in-line between two pipes and a neck portion associated with the conduit portion wherein the neck portion defines an opening providing access to the interior of the conduit portion, comprising:

a cover being securable to the neck portion for covering the access opening defined therein, the cover including at least one pierceable, self-closing stopper constructed of an elastomeric material and two platen members positioned in a face-to-face arrangement, each of said platen members having a central portion and a boundary portion bordering the central portion of the corresponding platen member, the central portion of each platen member defining a through-opening which is aligned with the through-opening of the other platen member and the central opening of the gasket means when said cover is operatively clamped to said neck portion, said stopper having a body of relatively small mass in comparison to the mass of the platen members and associated with said platen members so that the stopper body generally spans the aligned through-openings of the platen members and so that a hypodermic needle or the like can be directed through the stopper body and into the interior of said neck portion for the purpose of extracting a sample amount of fluid flowing through the conduit of said conduit-defining means, said stopper body having a platen portion and a nipple portion joined centrally of and extending from one side of the platen portion, the through-opening of one platen member snuggly accepting the nipple portion of the stopper body so that the stopper body is securely retained within said one platen member as surfaces of the nipple portion pressingly engage the walls of the through-opening of said one platen member, the central portion of the other platen member having a side face which generally faces said one platen member and including a detent in the form of a recess defined in said side face and located about the through-opening of said other platen member, said recess snuggly accepting the platen portion of the stopper body so that the stopper body is securely retained within said other platen member as surfaces of the platen portion pressingly engage the walls of the recess of said other platen member and so that the platen members are held in the aforesaid face-to-face arrangement and in an assembled condition as each platen member is retainably secured to the stopper.

12. The extention of claim 11 wherein the central portions of the platen members of said cover define a plurality of aligned through-openings disposed thereacross and there is one pierceable, self-closing stopper operatively associated with each one of said aligned through-openings so that each one of the aligned through-openings is spanned by a stopper and so that the platen members physically separate the stoppers from one another.

13. The invention of claim 11 wherein the conduit portion includes two straight end sections joined together at a right angle, each of said straight end sections terminating at a connection end adapted to be connected to a corresponding one of two pipes, and said neck portion is an extension of one of said end sections opposite the connection end of said one end section so that the conduit portion and said neck portion resemble a Tee fitting.

14. The invention of claim 13 wherein said neck portion includes an edge bordering said access opening and is relatively short in length as measured from the edge of the access opening.

* * * * *